United States Patent
Williams et al.

(10) Patent No.: US 7,857,748 B2
(45) Date of Patent: Dec. 28, 2010

(54) PHOTOCURABLE ENDOPROSTHESIS METHODS OF MANUFACTURE

(75) Inventors: Michael S. Williams, Santa Rosa, CA (US); Kevin D. Holbrook, Windsor, CA (US); Richard A. Glenn, Santa Rosa, CA (US); Jeffrey A. Smith, Santa Rosa, CA (US); Joseph M. DeSimone, Chapel Hill, NC (US)

(73) Assignee: Syne Cor, LLC, Durham, NC (US)

( * ) Notice: Subject to any disclaimer, the term of this patent is extended or adjusted under 35 U.S.C. 154(b) by 1052 days.

(21) Appl. No.: 11/584,784

(22) Filed: Oct. 19, 2006

(65) Prior Publication Data

US 2007/0038284 A1 Feb. 15, 2007

Related U.S. Application Data

(62) Division of application No. 10/342,771, filed on Jan. 15, 2003, now Pat. No. 7,141,061.

(51) Int. Cl.
*A61F 2/04* (2006.01)
*A61F 2/06* (2006.01)

(52) U.S. Cl. .............. 600/36; 623/1.21; 623/1.11; 430/320

(58) Field of Classification Search ........... 623/1.21
See application file for complete search history.

(56) References Cited

U.S. PATENT DOCUMENTS

| | | | | |
|---|---|---|---|---|
| 4,798,752 A * | 1/1989 | McLoughlin et al. | | 428/34.9 |
| 5,100,429 A * | 3/1992 | Sinofsky et al. | | 623/1.21 |
| 5,334,201 A * | 8/1994 | Cowan | | 623/1.21 |
| 5,344,444 A * | 9/1994 | Glastra | | 623/1.21 |
| 5,443,495 A * | 8/1995 | Buscemi et al. | | 623/1.21 |
| 5,464,419 A * | 11/1995 | Glastra | | 606/194 |
| 5,529,653 A * | 6/1996 | Glastra | | 156/216 |
| 5,591,199 A * | 1/1997 | Porter et al. | | 623/1.21 |
| 5,741,323 A * | 4/1998 | Pathak et al. | | 623/1.44 |
| 5,871,537 A * | 2/1999 | Holman et al. | | 623/1.23 |
| 5,899,917 A * | 5/1999 | Edwards et al. | | 606/195 |
| 5,997,570 A * | 12/1999 | Ligtenberg et al. | | 607/92 |
| 6,004,261 A * | 12/1999 | Sinofsky et al. | | 600/36 |
| 6,027,863 A * | 2/2000 | Donadio, III | | 430/320 |
| 6,395,326 B1 * | 5/2002 | Castro et al. | | 427/2.24 |
| 6,458,138 B1 * | 10/2002 | Sydney et al. | | 606/108 |
| 6,485,512 B1 * | 11/2002 | Cheng | | 623/1.21 |
| 6,887,266 B2 * | 5/2005 | Williams et al. | | 623/1.16 |
| 6,906,112 B1 * | 6/2005 | Wojciak et al. | | 522/18 |
| 6,994,723 B1 * | 2/2006 | McMahon | | 623/1.49 |
| 7,141,061 B2 * | 11/2006 | Williams et al. | | 623/1.11 |
| 7,147,660 B2 * | 12/2006 | Chobotov et al. | | 623/1.14 |
| 7,457,661 B2 * | 11/2008 | Doty | | 604/21 |
| 2002/0111673 A1 * | 8/2002 | Holton et al. | | 623/1.21 |
| 2003/0114914 A1 * | 6/2003 | Cheng | | 623/1.11 |

* cited by examiner

*Primary Examiner*—Paul Prebilic
(74) *Attorney, Agent, or Firm*—Deanna J. Shirley

(57) ABSTRACT

Methods of manufacture of endoprostheses comprising one or more photocurable materials are disclosed. The endoprostheses may comprise regions wherein the photocurable materials are selectively disposed about the endoprosthesis and are cured according to desired parameters to achieve varying desired properties. Photolithographic masking material may be selectively disposed about an inflatable balloon and exposed to a radiation emitting catheter.

11 Claims, 8 Drawing Sheets

PHOTOCURABLE ENDOPROSTHESIS METHODS OF MANUFACTURE

RELATED APPLICATIONS

This application is a divisional application of U.S. patent application Ser. No. 10/342,771, by Williams, et al., entitled "Photocurable Endoprostheses and Method of Manufacture", filed Jan. 15, 2003, now U.S. Pat. No. 7,141,061 and is related to Provisional U.S. Patent Application Ser. No. 60/426,734 filed Nov. 15, 2002; U.S. patent application Ser. No. 10/342, 748 filed Jan. 15, 2003, by Williams, et al., entitled "Polymeric Endoprostheses and Methods of Manufacture; and U.S. patent application Ser. No. 10/342,622, filed Jan. 15, 2003, by Williams, et al., entitled "Endoprostheses and Methods of Manufacture, now U.S. Pat. No. 6,887,266 to Williams et al.; Provisional U.S. Patent Application Ser. No. 60/426,898 entitled "Polymeric Endoprostheses and Methods of Manufacture", to Williams, et al., Provisional U.S. Patent Application Ser. No. 60/426,737, entitled "Improved Endoprostheses and Methods of Manufacture", to Williams et al., Provisional U.S. Patent Application Ser. No. 60/426,126 entitled "Carbon Dioxide-Assisted Methods of Providing Biocompatible Intraluminal Prostheses", to Williams, et al., and Provisional U.S. Patent Application Ser. No. 60/426,125 entitled "Intraluminal Prostheses and Carbon Dioxide-Assisted Methods of Impregnating Same with Pharmacological Agents" to Williams, et al.". The above applications are commonly owned. All of the above applications are hereby incorporated by reference, each in its entirety.

FIELD OF THE INVENTION

The invention herein relates generally to medical devices and the manufacture thereof, and more particularly to improved endoprostheses for use in the treatment of strictures in lumens of the body.

BACKGROUND OF THE INVENTION

Ischemic heart disease is the major cause of death in industrialized countries. Ischemic heart disease, which often results in myocardial infarction, is a consequence of coronary atherosclerosis. Atherosclerosis is a complex chronic inflammatory disease and involves focal accumulation of lipids and inflammatory cells, smooth muscle cell proliferation and migration, and the synthesis of extracellular matrix. *Nature* 1993; 362:801-809. These complex cellular processes result in the formation of atheromatous plaque, which consists of a lipid-rich core covered with a collagen-rich fibrous cap, varying widely in thickness. Further, plaque disruption is associated with varying degrees of internal hemorrhage and luminal thrombosis because the lipid core and exposed collagen are thrombogenic. *J Am Coll Cardiol*. 1994; 23:1562-1569 Acute coronary syndrome usually occurs as a consequence of such disruption or ulceration of a so called "vulnerable plaque". *Arterioscler Thromb Vasc Biol*. Volume 22, No. 6, June 2002, p. 1002.

In addition to coronary bypass surgery, a current treatment strategy to alleviate vascular occlusion includes percutaneous transluminal coronary angioplasty, expanding the internal lumen of the coronary artery with a balloon. Roughly 800,000 angioplasty procedures are performed in the U.S. each year (*Arteriosclerosis, Thrombosis, and Vascular Biology* Volume 22, No. 6, June 2002, p. 884). However, 30% to 50% of angioplasty patients soon develop significant restenosis, a narrowing of the artery through migration and growth of smooth muscle cells.

In response to the significant restenosis rate following angioplasty, percutaneously placed endoprostheses have been extensively developed to maintain fluid flow through a diseased coronary artery. Such endoprostheses, or stents, which have been traditionally fabricated using metal alloys, include self-expanding or balloon-expanded devices that are "tracked" through the vasculature and deployed proximate one or more lesions. Stents considerably enhance the long-term benefits of angioplasty, but 10% to 50% of patients receiving stents still develop restenosis. (*J Am Coll Cardiol*. 2002; 39:183-193. Consequently, a significant portion of the relevant patient population undergoes continued monitoring and, in many cases, additional treatment.

Continued improvements in stent technology aim at producing easily tracked, easily visualized and readily deployed stents, which exhibit the requisite radial strength without sacrificing a small delivery profile and sufficient flexibility to traverse the diseased human vasculature. Further, numerous therapies directed to the cellular mechanisms of accumulation of inflammatory cells, smooth muscle cell proliferation and migration show tremendous promise for the successful long-term treatment of ischemic heart disease. Consequently, advances in coupling delivery of such therapies to the mechanical support of vascular endoprostheses, delivered proximate the site of disease, offer great hope to the numerous individuals suffering heart disease.

While advances in the understanding of ischemic heart disease as a complex chronic inflammatory process take place, traditional diagnostic techniques such as coronary angiography yield to next generation imaging modalities. In fact, coronary angiography may not be at all useful in identifying inflamed atherosclerotic plaques that are prone to producing clinical events. Imaging based upon temperature differences, for example, are undergoing examination for use in detecting coronary disease. Magnetic resonance imaging (MRI) is currently emerging as the state of the art diagnostic arterial imaging, enhancing the detection, diagnosis and monitoring of the formation of vulnerable plaques. Transluminal intervention guided by MRI is expected to follow. However, metals produce distortion and artifacts in MR images, rendering use of the traditionally metallic stents in coronary, biliary, esophageal, ureteral, and other body lumens incompatible with the use of MRI.

Consequently, an emerging clinical need for interventional devices that are compatible with and complementary to new imaging modalities is evident. Further, devices that exhibit improved trackability to previously undetectable disease within remote regions of the body, especially the coronary vasculature are needed. And finally, devices that both exhibit improved mechanical support and are readily compatible with adjunct therapies in order to lower or eliminate the incidence of restenosis are needed.

SUMMARY OF THE INVENTION

A method of manufacture of an endoprosthesis is disclosed which may comprise the steps of providing an endoprosthesis having a first curable material, a first region and a second region, wherein the first curable material is curable by exposure to a radiation source; providing a radiation emitting catheter comprising an inflatable balloon, wherein the balloon comprises a photolithographic masking coating to prevent the exposure of said first region of said endoprosthesis to radiation; and selectively curing the first curable material. The endoprosthesis may further comprise a second curable material. The method may further comprise the steps of placing the endoprosthesis a body lumen and selectively exposing said endoprosthesis to radiation.

The step of selectively exposing the endoprosthesis to radiation may further comprise the steps of inflating the balloon within the endoprosthesis and allowing the radiation emitting catheter to emit radiation, whereby the endoprosthesis is selectively exposed to radiation by the photolithographic masking coating.

A method of manufacture of an endoprosthesis according to the invention may comprise providing a balloon catheter having a balloon; inflating the balloon to nominal pressure; applying a photolithographic masking coating to the balloon in a predetermined pattern; applying a photocurable film over the balloon; introducing a radiation source within the balloon; curing said film at a first wavelength; removing non-cured material; deflating the balloon; packaging and sterilizing the endoprosthesis and balloon catheter; inserting the endoprosthesis into the vasculature of a patient; inflating the balloon proximate a lesion; curing the prosthesis at a second wavelength; deflating the balloon; and removing the balloon catheter. The predetermined pattern may comprise a negative image of an endoprosthesis to be cured in stages on the balloon. Further, the first wavelength may be in a range of between 320 and 350 nm and the second wavelength may be in a range of between 365 and 400 nm.

A method of manufacture according to the invention may comprise the steps of coextruding a first curable material and a second curable material to form a generally tubular structure; cutting portions from said tube to define a desired pattern; and initiating curing of said first curable material and said second curable material. The first curable material may cure by exposure to radiation at a first wavelength, and the second curable material may cure by exposure to radiation at a second wavelength, and the method may further comprise the additional steps of selectively exposing the extruded tube to radiation at the first wavelength, and selectively exposing the extruded tube to radiation at the second wavelength. The first wavelength may be between 320 and 350 nm and the second wavelength may be between 365 and 400 nm. The step of selectively exposing the extruded tube to radiation at a first wavelength may comprise placing the endoprosthesis within a body lumen; providing a balloon catheter and inflating the balloon to nominal pressure; introducing a radiation emitting device; activating the radiation device to cure material at the first wavelength; activating the radiation device to cure material at the second wavelength; and removing the catheter from the body lumen.

DETAILED DESCRIPTION OF THE INVENTION

Figure 1A:
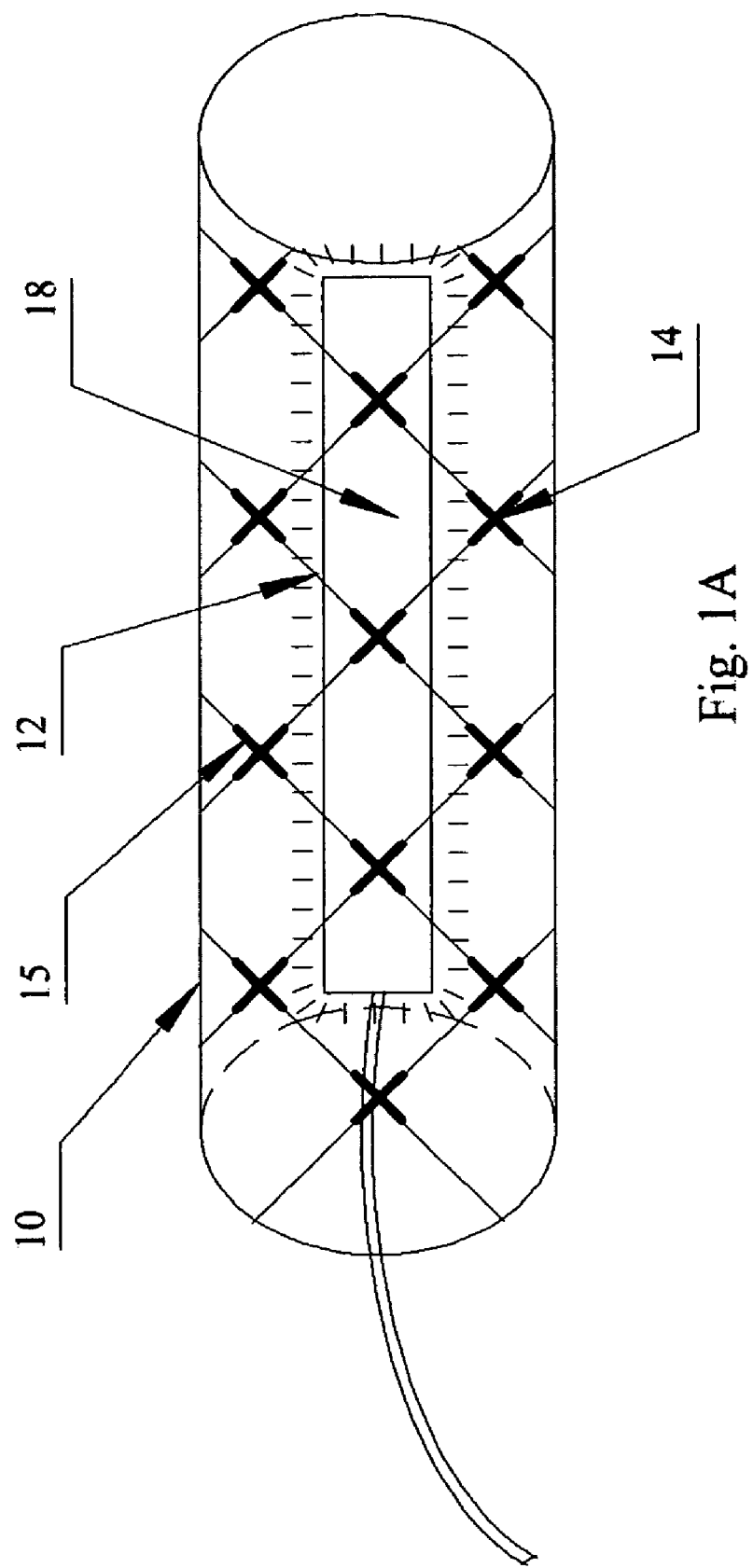
FIGS. 1A-B are plan views of an embodiment according to the invention during and after photocuring.

Although the invention herein is not limited as such, some embodiments of the invention comprise materials that are erodible. "Erodible" refers to the ability of a material to maintain its structural integrity for a desired period of time, and thereafter gradually undergo any of numerous processes whereby the material substantially loses tensile strength and mass. Examples of such processes comprise hydrolysis, enzymatic and non-enzymatic degradation, oxidation, enzymatically-assisted oxidation, and others, thus including bioresorption, dissolution, and mechanical degradation upon interaction with a physiological environment into components that the patient's tissue can absorb, metabolize, respire, and/or excrete. Polymer chains are cleaved by hydrolysis and are eliminated from the body through the Krebs cycle, primarily as carbon dioxide and in urine. "Erodible" and "degradable" are intended to be used interchangeably herein.

The term "endoprosthesis" refers to any prosthetic device placed within a body lumen or duct to in order to therapeutically treat the body lumen or duct, including but limited to the objective of restoring or enhancing flow of fluids through a body lumen or duct.

A "self-expanding" endoprosthesis has the ability to revert readily from a reduced profile configuration to a larger profile configuration in the absence of a restraint upon the device that maintains the device in the reduced profile configuration.

"Balloon expandable" refers to a device that comprises a reduced profile configuration and an expanded profile configuration, and undergoes a transition from the reduced configuration to the expanded configuration via the outward radial force of a balloon expanded by any suitable inflation medium.

The term "balloon assisted" refers to a self-expanding device the final deployment of which is facilitated by an expanded balloon.

The term "fiber" refers to any generally elongate member fabricated from any suitable material, whether polymeric, metal or metal alloy, natural or synthetic.

As used herein, a device is "implanted" if it is placed within the body to remain for any length of time following the conclusion of the procedure to place the device within the body.

The term "diffusion coefficient" refers to the rate by which a substance elutes, or is released either passively or actively from a substrate.

As used herein, the term "braid" refers to any braid or mesh or similar woven structure produced from between 1 and several hundred longitudinal and/or transverse elongate elements woven, braided, knitted, helically wound, or intertwined any manner, at angles between 0 and 180 degrees and usually between 45 and 105 degrees, depending upon the overall geometry and dimensions desired.

Unless specified, suitable means of attachment may include by melt bond, chemical bond, adhesive, sintering, welding, or any means known in the art.

"Shape memory" refers to the ability of a material to undergo structural phase transformation such that the material may define a first configuration under particular physical and/or chemical conditions, and to revert to an alternate configuration upon a change in those conditions. Shape memory materials may be metal alloys including but not limited to nickel titanium, or may be polymeric. A polymer is a shape memory polymer if the original shape of the polymer is recovered by heating it above a shape recovering temperature (defined as the transition temperature of a soft segment) even if the original molded shape of the polymer is destroyed mechanically at a lower temperature than the shape recovering temperature, or if the memorized shape is recoverable by application of another stimulus. Such other stimulus may include but is not limited to pH, salinity, hydration, and others. Some embodiments according to the invention may comprise one or more polymers having a structure that assumes a first configuration, a second configuration, and a hydrophilic polymer of sufficient rigidity coated upon at least a portion of the structure when the device is in the second configuration. Upon placement of the device in an aqueous environment and consequent hydration of the hydrophilic polymer, the polymer structure reverts to the first configuration.

As used herein, the term "segment" refers to a block or sequence of polymer forming part of the shape memory polymer. The terms hard segment and soft segment are relative terms, relating to the transition temperature of the segments. Generally speaking, hard segments have a higher glass transition temperature than soft segments, but there are exceptions. Natural polymer segments or polymers include but are not limited to proteins such as casein, gelatin, gluten, zein, modified zein, serum albumin, and collagen, and polysaccharides such as alginate, chitin, celluloses, dextrans, pullulane, and polyhyaluronic acid; poly(3-hydroxyalkanoate)s, especially poly(.beta.-hydroxybutyrate), poly(3-hydroxyoctanoate) and poly(3-hydroxyfatty acids).

Representative natural erodible polymer segments or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Suitable synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof.

Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, arboxymethyl cellulose, cellulose triacetate and cellulose sulfate sodium salt. These are collectively referred to herein as "celluloses".

Examples of synthetic degradable polymer segments or polymers include polyhydroxy acids, such as polylactides, polyglycolides and copolymers thereof; poly(ethylene terephthalate); poly(hydroxybutyric acid); poly(hydroxyvaleric acid); poly[lactide-co-(.epsilon.-caprolactone)]; poly[glycolide-co-(.epsilon.-caprolactone)]; polycarbonates, poly(pseudo amino acids); poly(amino acids); poly(hydroxyalkanoate)s; polyanhydrides; polyortho esters; and blends and copolymers thereof.

For those embodiments comprising a shape memory polymer, the degree of crystallinity of the polymer or polymeric block(s) is between 3 and 80%, more often between 3 and 65%. The tensile modulus of the polymers below the transition temperature is typically between 50 MPa and 2 GPa (gigapascals), whereas the tensile modulus of the polymers above the transition temperature is typically between 1 and 500 MPa. Most often, the ratio of elastic modulus above and below the transition temperature is 20 or more.

The melting point and glass transition temperature of the hard segment are generally at least 10 degrees C., and preferably 20 degrees C., higher than the transition temperature of the soft segment. The transition temperature of the hard segment is preferably between −60 and 270 degrees C., and more often between 30 and 150 degrees C. The ratio by weight of the hard segment to soft segments is between about 5:95 and 95:5, and most often between 20:80 and 80:20. The shape memory polymers contain at least one physical crosslink (physical interaction of the hard segment) or contain covalent crosslinks instead of a hard segment. The shape memory polymers can also be interpenetrating networks or semi-interpenetrating networks.

Rapidly erodible polymers such as poly(lactide-co-glycolide)s, polyanhydrides, and polyorthoesters, which have carboxylic groups exposed on the external surface as the smooth surface of the polymer erodes, also can be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

Examples of suitable hydrophilic polymers include but are not limited to poly(ethylene oxide), polyvinyl pyrrolidone, polyvinyl alcohol, poly(ethylene glycol), polyacrylamide poly(hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof.

Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of melting even when the polymers are not hydrated. Either type of polymeric block can be used, depending on the desired application and conditions of use.

Curable materials include any material capable of being able to transform from a fluent or soft material to a harder material, by cross-linking, polymerization, or other suitable process. Materials may be cured over time, thermally, chemically, or by exposure to radiation. For those materials that are cured by exposure to radiation, many types of radiation may be used, depending upon the material. Wavelengths in the spectral range of about 100-1300 nm may be used. The material should absorb light within a wavelength range that is not readily absorbed by tissue, blood elements, physiological fluids, or water. Ultraviolet radiation having a wavelength ranging from about 100-400 nm may be used, as well as visible, infrared and thermal radiation. The following materials are some examples of curable materials: urethanes, polyurethane oligomer mixtures, acrylate monomers, aliphatic urethane acrylate oligomers, acrylamides, UV curable epoxies, photopolymerizable polyanhydrides and other UV curable monomers. Alternatively, the curable material can be a material capable of being chemically cured, such as silicone based compounds which undergo room temperature vulcanization. Alternatively, photocurable polyanhydrides solids are desirable. When cured at approximately 365 nm, less than 1% free monomer remains.

Some embodiments according to the invention comprise materials that are cured in a desired pattern. Such materials may be cured by any of the foregoing means. Further, for those materials that are photocurable, such a pattern may be created by coating the material in a negative image of the desired pattern with a masking material using standard photoresist technology. Absorption of both direct and incident radiation is thereby prevented in the masked regions, curing the device in the desired pattern. A variety of biocompatibly eroding coating materials may be used, including but not limited to gold, magnesium, aluminum, silver, copper, platinum, inconel, chrome, titanium indium, indium tin oxide. Projection optical photolithography systems that utilize the vacuum ultraviolet wavelengths of light below 240 nm provide benefits in terms of achieving smaller feature dimensions. Such systems that utilize ultraviolet wavelengths in the 193 nm region or 157 nm wavelength region have the potential of improving precision masking devices having smaller feature sizes.

Photopolymerization of multifunctional monomers readily allows for the production of high density crosslinked polymer networks having increased thermal stabililty, mechanical strenth, and resistance to solvent absorption. Additionally, photopolymerization can be performed in a matter of between seconds and minutes, conferring great clinical advantages, and control over the extent of polymerization desired. Endoprostheses fabricated utilizing photopolymerization thereby can transition rapidly and to a desired extent from a nearly liquid, highly flexible (and therefore easily tracked) form to a semi-rigid, stable, device exhibiting the requisite radial strength. Additionally, regions of endoprostheses can be selectively photopolymerized to achieve desired physical characteristics that vary from the physical characteristics of other regions of the device. For example, middle portions of an endoprosthesis where a high degree of structural rigidity is desired may be selectively photopolymerized to achieve a higher cross-linking density than the outer end portions, which may be desired to be more highly compliant. As another example, structural support members may be selectively photopolymerized to achieve greater structural rigidity than, for example, longitudinal connecting members. Materials may be selected for the wavelength at which they polymerize, and an endoprosthesis fabricated from materials at varied wavelengths disposed in regions according to the desired physical properties of the region. Examples of multifunctional monomers include diethylene glycol dimethacrylate, methacrylated 1,6-bis(carboxyphenoxy)hexane, and methacrylated pyromellitylimidoalanine.

Though not limited thereto, some embodiments according to the invention have been surface treated to comprise one or more therapeutic substances that will elute from the structure or prosthesis independently or as the material comprising the stent erodes. The diffusion coefficient of various regions of an endoprosthesis, for example, a luminal surface, may be varied according to the desired diffusion coefficient of a particular surface. Alternatively, therapeutic substances may be incorporated into the materials that comprise the endoprosthesis. According to the invention, such surface treatment and/or incorporation of therapeutic substances may be performed utilizing one or more of numerous processes that utilize carbon dioxide fluid, e.g., carbon dioxide in a liquid or supercritical state.

A supercritical fluid is a substance above its critical temperature and critical pressure (or "critical point"). Compressing a gas normally causes a phase separation and the appearance of a separate liquid phase. However, all gases have a critical temperature above which the gas cannot be liquefied by increasing pressure, and a critical pressure or pressure which is necessary to liquefy the gas at the critical temperature. For example, carbon dioxide in its supercritical state exists as a form of matter in which its liquid and gaseous states are indistinguishable from one another. For carbon dioxide, the critical temperature is about 31 degrees C. (88 degrees D) and the critical pressure is about 73 atmospheres or about 1070 psi.

The term "supercritical carbon dioxide" as used herein refers to carbon dioxide at a temperature greater than about 31 degrees C. and a pressure greater than about 1070 psi. Liquid carbon dioxide may be obtained at temperatures of from about −15 degrees C. to about −55 degrees C. and pressures of from about 77 psi to about 335 psi. One or more solvents and blends thereof may optionally be included in the carbon dioxide. Illustrative solvents include, but are not limited to, tetrafluoroisopropanol, chloroform, tetrahydrofuran, cyclohexane, and methylene chloride. Such solvents are typically included in an amount, by weight, of up to about 20%.

In general, carbon dioxide may be used to effectively lower the glass transition temperature of a polymeric material to facilitate the infusion of pharmacological agent(s) into the polymeric material. Such agents include but are not limited to hydrophobic agents, hydrophilic agents and agents in particulate form. For example, following fabrication, an endoprosthesis and a hydrophobic pharmacological agent may be immersed in supercritical carbon dioxide. The supercritical carbon dioxide "plasticizes" the polymeric material, that is, it allows the polymeric material to soften at a lower temperature, and facilitates the infusion of the pharmacological agent into the polymeric endoprosthesis or polymeric coating of a stent at a temperature that is less likely to alter and/or damage the pharmacological agent.

As an additional example, an endoprosthesis and a hydrophilic pharmacological agent can be immersed in water with an overlying carbon dioxide "blanket". The hydrophilic pharmacological agent enters solution in the water, and the carbon dioxide "plasticizes" the polymeric material, as described above, and thereby facilitates the infusion of the pharmacological agent into a polymeric endoprosthesis or a polymeric coating of an endoprosthesis.

As yet another example, carbon dioxide may be used to "tackify", or render more fluent and adherent a polymeric endoprosthesis or a polymeric coating on an endoprosthesis to facilitate the application of a pharmacological agent thereto in a dry, micronized form. A membrane-forming polymer, selected for its ability to allow the diffusion of the pharmacological agent therethrough, may then applied in a layer over the endoprosthesis. Following curing by suitable means, a membrane that permits diffusion of the pharmacological agent over a predetermined time period forms.

In alternative embodiments of the present invention, at least one monomer or comonomer can be solubilized in carbon dioxide and copolymerized with a fluoromonomer. Any suitable monomers or comonomers can be employed, including, but not limited to, acrylate, methacrylate, acrylamide, methacrylamide, styrenics, ethylene, and vinyl ether monomers. The copolymerizations of the present invention may be carried out under temperature and pressure conditions similar to those given above.

Objectives of therapeutics substances incorporated into materials forming or coating an endoprosthesis according to the invention include reducing the adhesion and aggregation of platelets at the site of arterial injury, block the expression of growth factors and their receptors; develop competitive antagonists of growth factors, interfere with the receptor signaling in the responsive cell, promote an inhibitor of smooth muscle proliferation. Anitplatelets, anticoagulants, antineoplastics, antifibrins, enzymes and enzyme inhibitors, antimitotics, antimetabolites, anti-inflammatories, antithrombins, antiproliferatives, antibiotics, and others may be suitable. More specific examples of the foregoing examples are set forth in related Patent Application Ser. No. 60/426,125 and are incorporated herein.

Figure 1B:
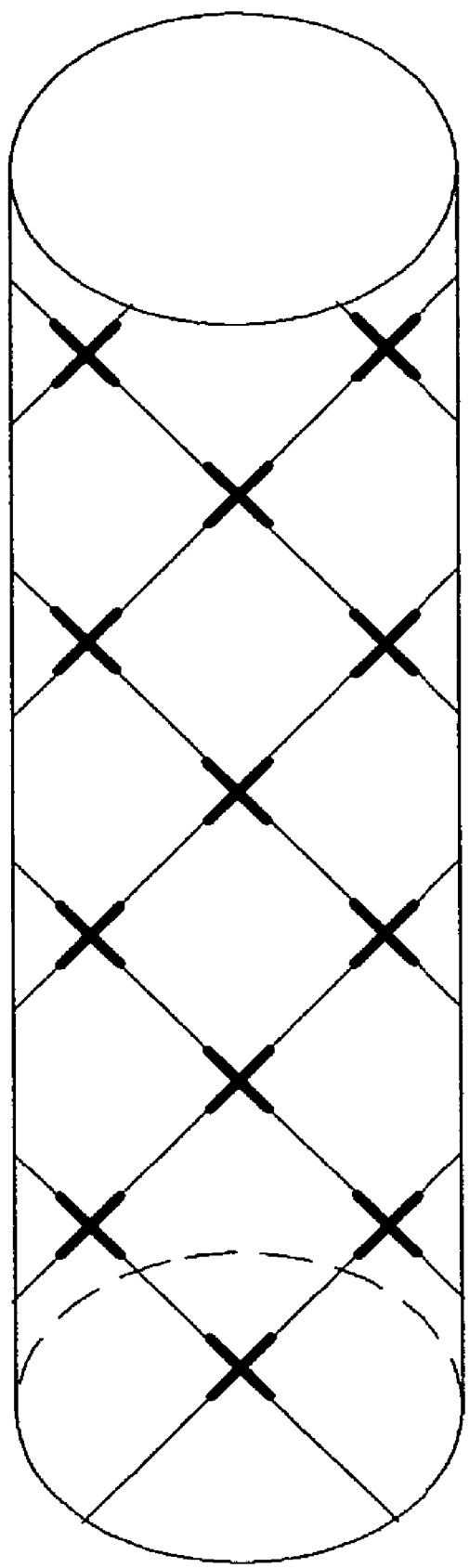

FIGS. 1A-B represent plan views of another embodiment according to the invention. Endoprosthesis 10 of FIGS. 1A-B, shown in its expanded configuration, comprises a generally tubular structure formed from one or more fibers 12. One or more fibers 12 comprise fiber points of intersection 14. Prior to deployment, fibers 12 comprise a photo-curable coating 15, at or near points of intersection 14, in semi-cured form. Following delivery and expansion of the endoprosthesis 10 by suitable means, the delivery catheter (not shown) is replaced by ultraviolet light delivery catheter 18. Ultraviolet radiation within the ranges discussed above is delivered via ultraviolet light delivery catheter 18, and photocurable coating 15 is cured. Ultraviolet light delivery catheter 18 is then removed from the vessel, and endoprosthesis 10 is left in place.

Figure 2:
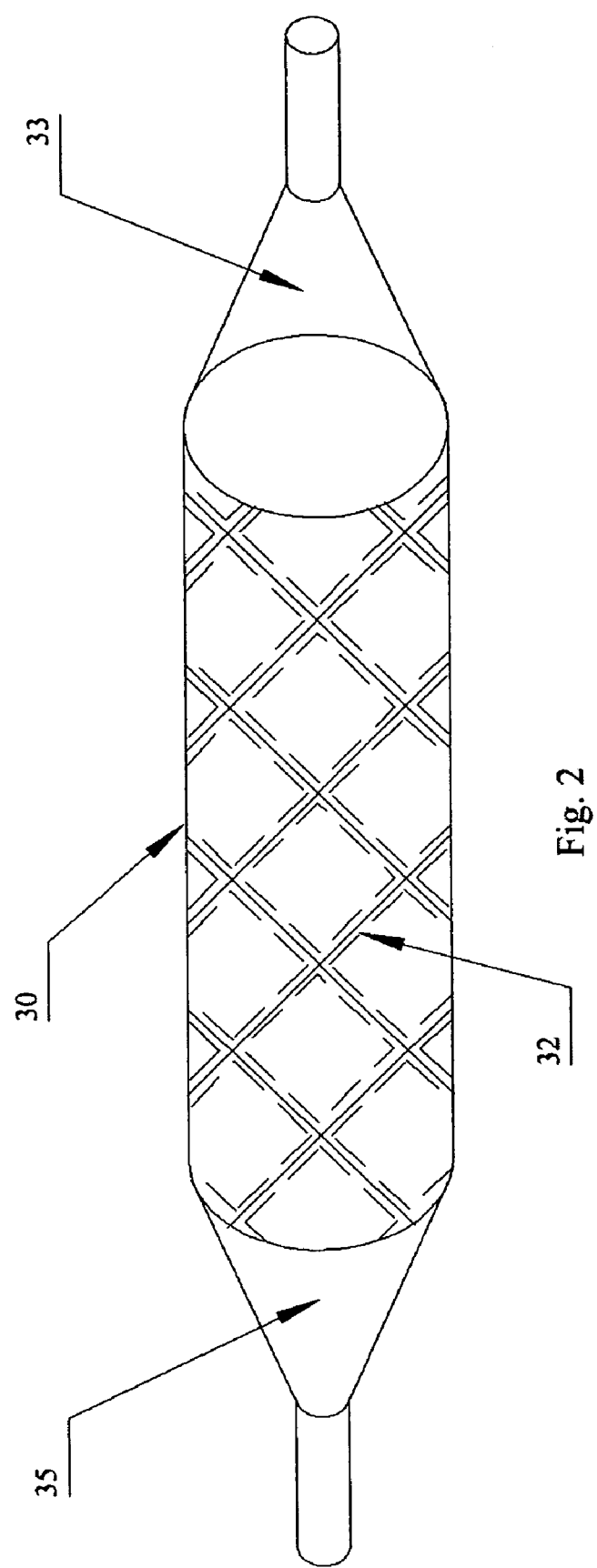
FIG. 2 is a plan view of alternative embodiment according to the invention.

Alternatively, substantially the entire endoprosthesis may comprise a photocurable coating. As shown in FIG. 2, endoprosthesis 30 may be disposed on distal end 33 of expanded balloon 35, over which photolithographic masking material 32 has been applied in a pattern. Masking material 32 prevents the delivery of radiation, to leave desired portions, for example fiber points of intersection, exposed. Endoprosthesis 30 may then be exposed to ultraviolet or other suitable form of radiation, allowing the exposed portions of the coated device to cure. Following delivery of radiation, balloon 35 is removed. In time, the photolithographic masking material, and eventually endoprosthesis 30 may erode biocompatibly.

Figure 3:
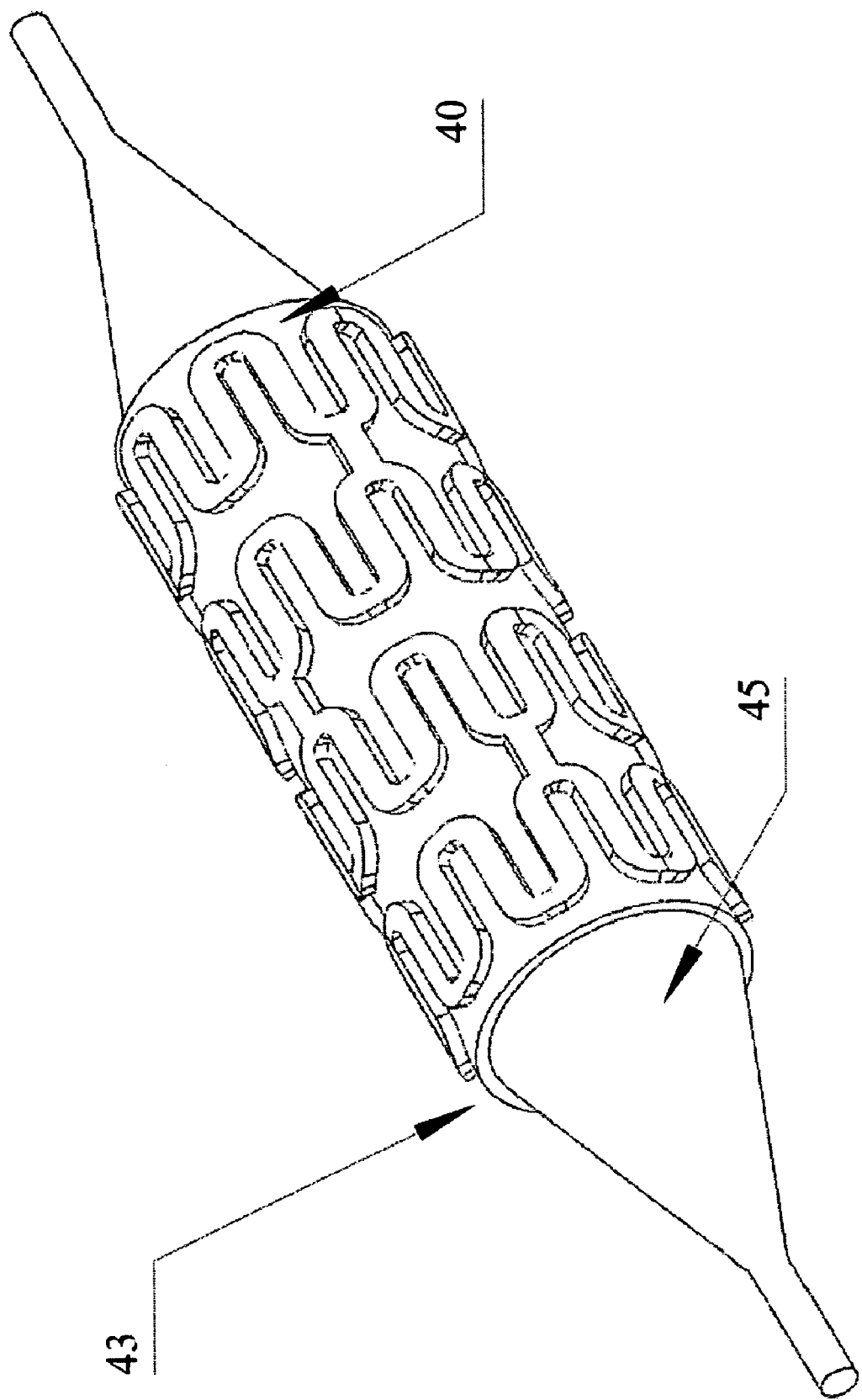
FIG. 3 is a plan view of yet another embodiment according to the invention.

An alternative embodiment according to the invention is shown in FIG. 3. As discussed above with respect to FIG. 2, endoprosthesis 40 is mounted upon distal end 43 of balloon 45, which has been coated with photolithographic masking material in a pattern such radiation is selectively delivered to endoprosthesis 40, allowing curing in selected regions of endoprosthesis 40.

In an alternative embodiment, an endoprosthesis can comprise multiple materials that are curable at different wavelengths, in order to confer varied physical properties on the prosthesis according to the desired properties of a particular region of the endoprosthesis. For example, the proximal and distal ends of a prosthesis can comprise one or more materials that are curable at a wavelength distinct from that at which the remainder of the prosthesis is curable, and can be selected for greater compliance. It has been shown clinically that restenosis occurs in response to vessel trauma at the proximal and distal ends of prostheses. By controlling the physical properties to enhance flexibility and to minimize compliance mismatch at the proximal and distal ends of the prosthesis, tremendous clinical benefit can be conferred upon the device. As a second example, the material selected to comprise the longitudinal connecting members can cure at a different wavelength than that at which the remainder of the prosthesis cures, to impart greater compliance and flexibility of longitudinal members while allowing the structural rigidity needed in support members.

Figure 4:
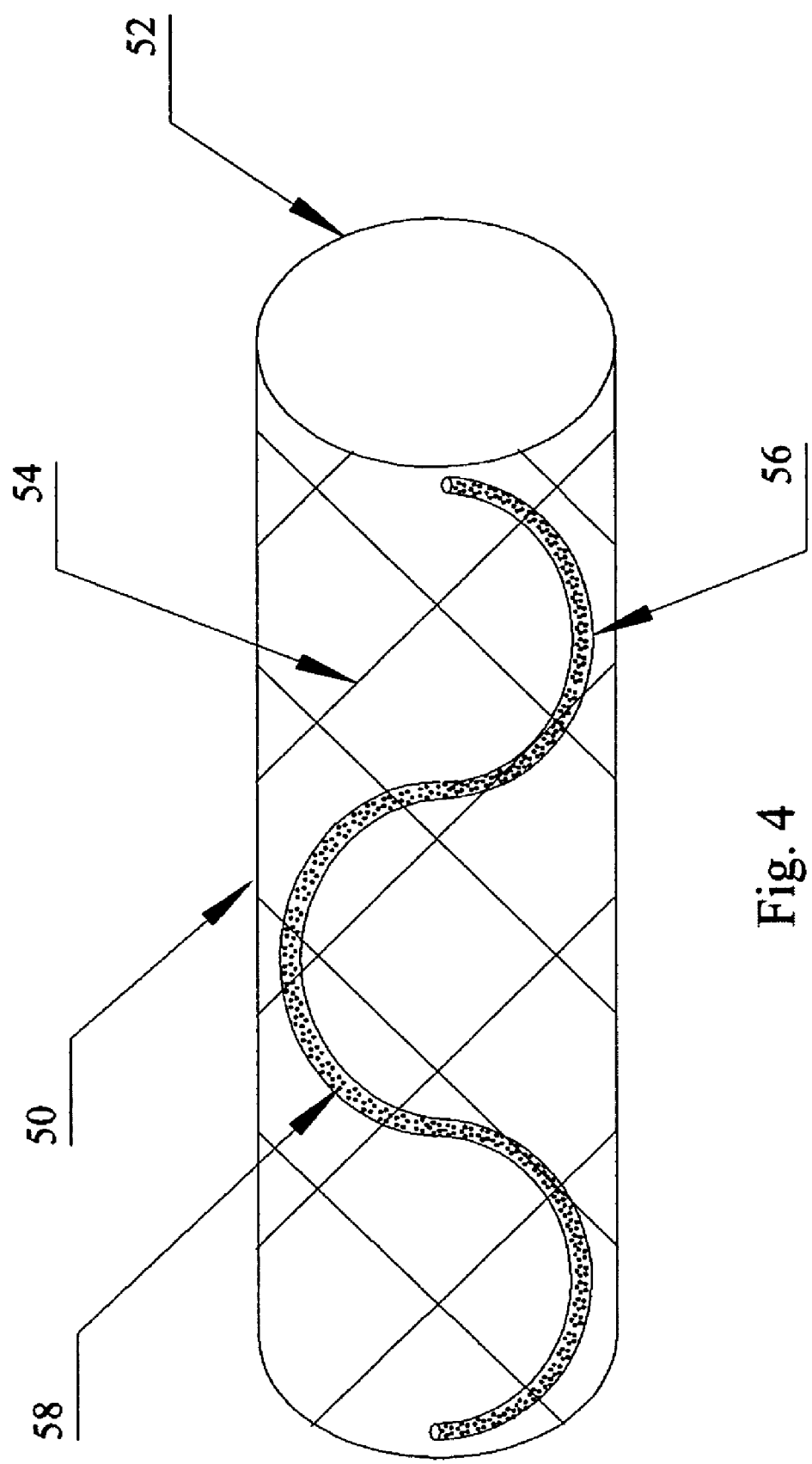
FIG. 4 is a plan view of still another embodiment according to the invention.

Turning now to FIG. 4, a further embodiment according to the invention is provided. Endoprosthesis 50 comprises a generally tubular element 52. Although alternative configurations are possible, generally tubular element 52 is formed by weaving, as defined above, one or more fibers 54. Hollow element 56 is then woven or affixed to generally tubular element 52. Hollow element 56 comprises curable material 58 in its interior. Following expansion of endoprosthesis 50, curable material 58 is allowed to cure or, if it is photocurable, is exposed to radiation in order to initiate curing. Hollow element 56, following curing of curable material 58, confers structural support upon endoprosthesis 50.

Figure 5A:
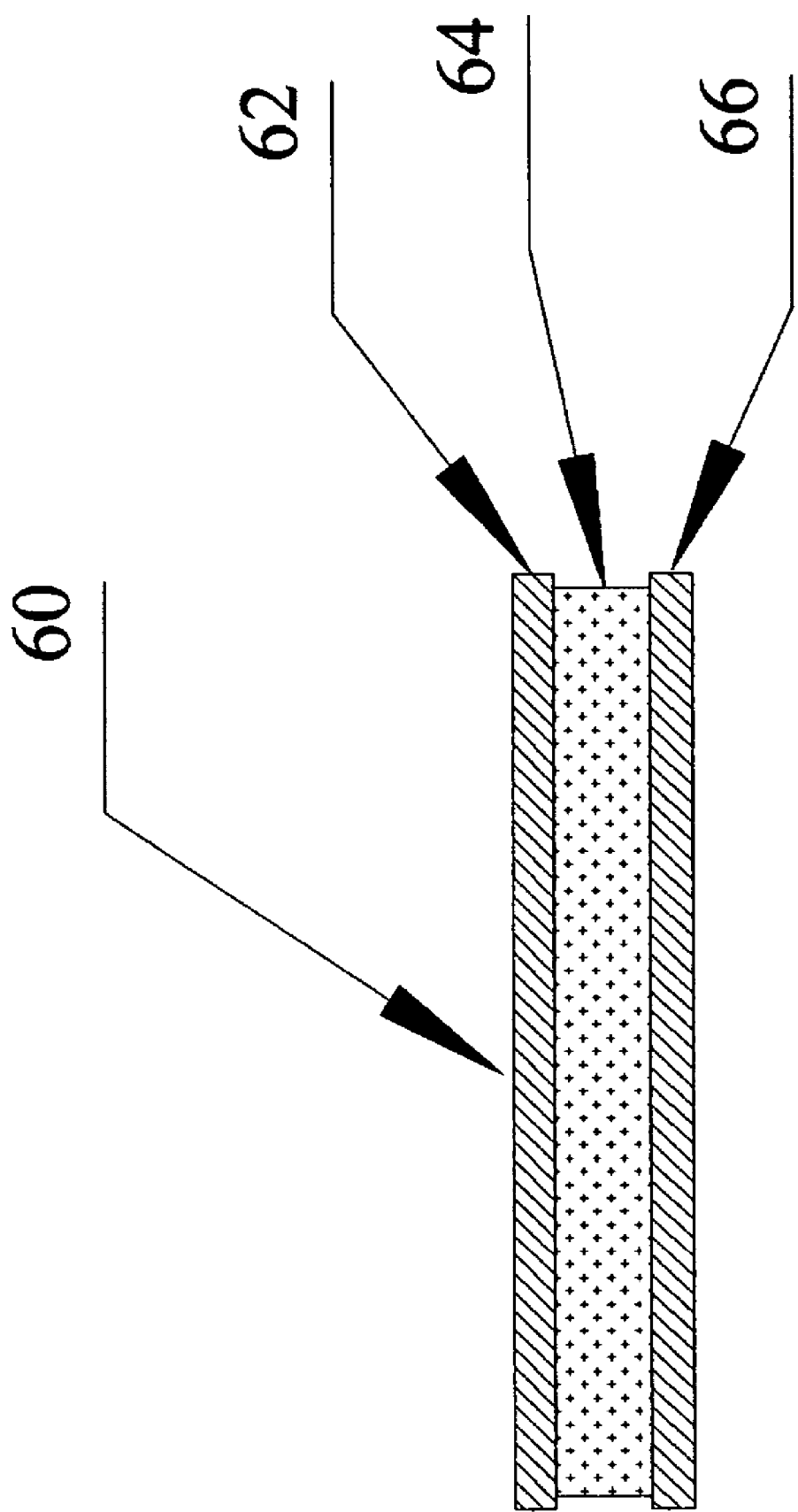
FIGS. 5A-C illustrate a series of steps in the manufacture of an alternative embodiment according to the invention.
Figure 5B:
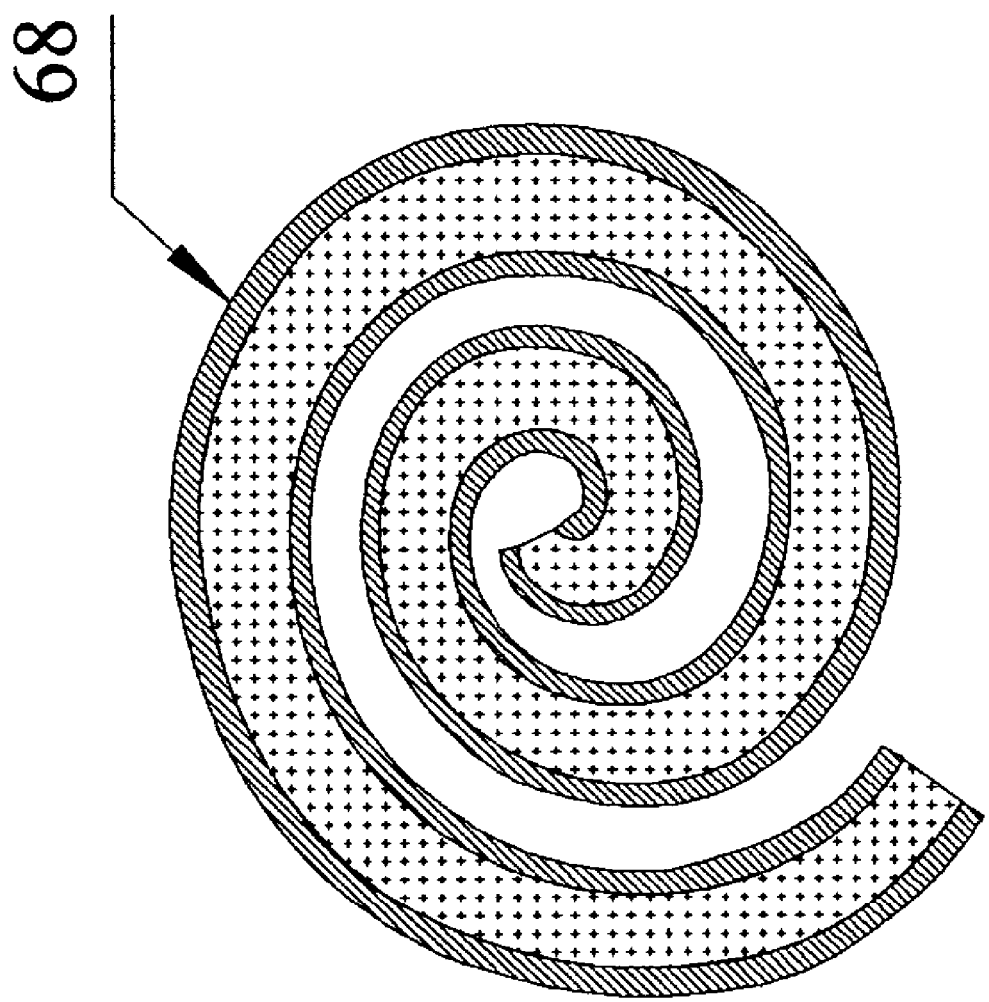
Figure 5C:
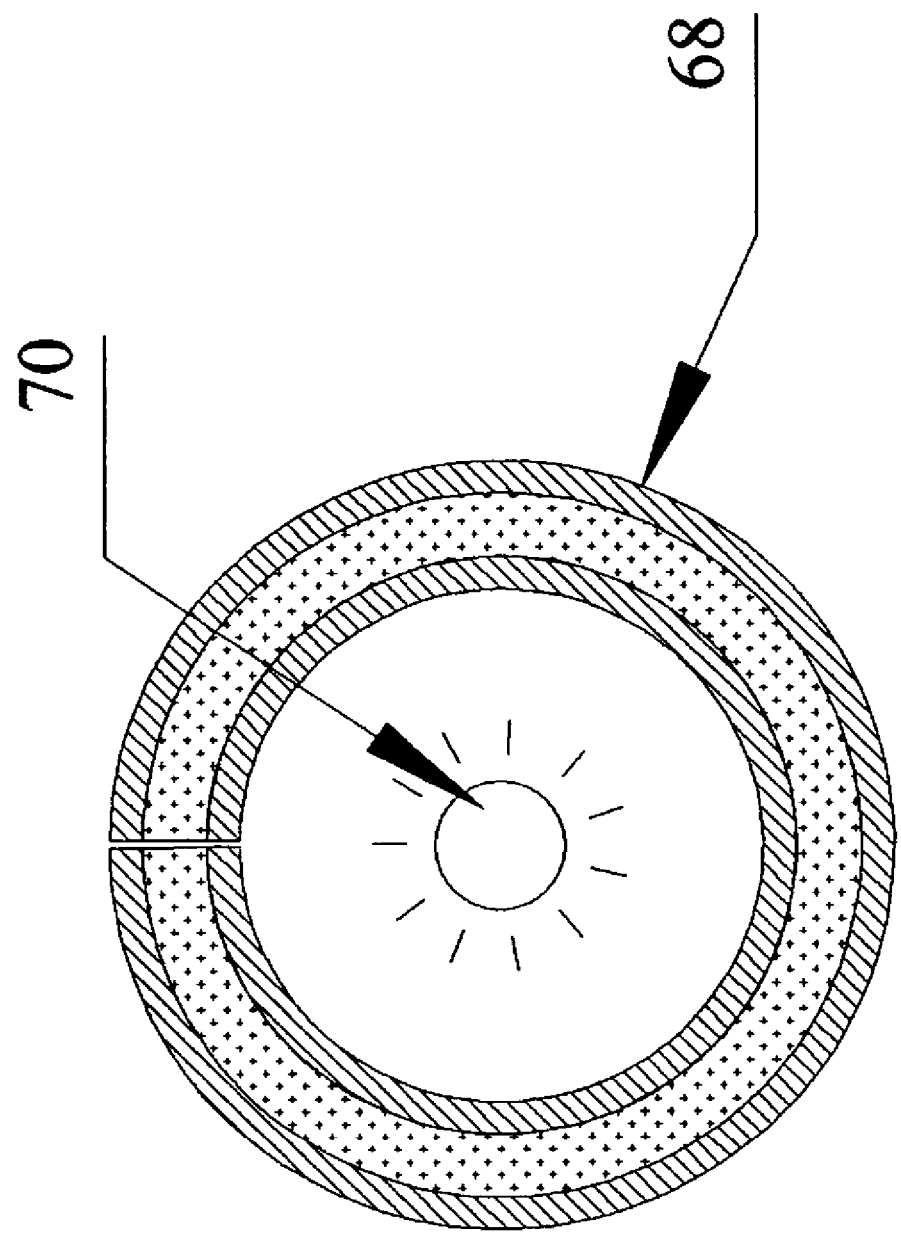

FIGS. 5A-C represent steps in the preparation of an alternative embodiment according to the invention. FIG. 5A is an enlarged end view of composite flat sheet 60. Composite flat sheet 60 comprises a first polymeric laminate layer 62, a photocurable and/or chemically reactive membrane 64, and second polymeric laminate layer 66. After formation of composite flat sheet 60, it is rolled to form unexpanded endoprosthesis 68, as shown in FIG. 5B. Upon expansion of endoprosthesis 68, light delivery source 70 is introduced within endoprosthesis 68, as seen in an end view in FIG. 5C. Photocurable and/or chemically reactive membrane 64 is thereby cured, conferring the requisite structural rigidity to endoprosthesis 68.

While particular forms of the invention have been illustrated and described above, the foregoing descriptions are intended as examples, and to one skilled in the art will it will be apparent that various modifications can be made without departing from the spirit and scope of the invention.

We claim:

1. A method of manufacture of an endoprosthesis comprising the steps of:
    providing an endoprosthesis comprising a first curable material, a first region and a second region, wherein said first curable material is curable by exposure to a radiation source;
    providing a radiation emitting catheter comprising an inflatable balloon, wherein said balloon comprises a photolithographic masking coating to prevent the exposure of said first region of said endoprosthesis to radiation;
    selectively curing said first curable material.

2. The method of claim 1 wherein said endoprosthesis further comprises a second curable material.

3. The method of claim 1 further comprising the steps of:
    placing said endoprosthesis within a body lumen;
    selectively exposing said endoprosthesis to radiation.

4. The method of claim 3 wherein said step of selectively exposing said endoprosthesis to radiation further comprises:
    inflating said balloon within said endoprosthesis;
    allowing said radiation emitting catheter to emit radiation, whereby said endoprosthesis is selectively exposed to radiation by the photolithographic masking coating.

5. A method of manufacture of an endoprosthesis comprising:
    providing a balloon catheter comprising a balloon;
    inflating said balloon to nominal pressure;
    applying a photolithographic masking coating to said balloon in a predetermined pattern;
    applying a photocurable film over said balloon;
    introducing a radiation source within said balloon;
    curing said film at a first wavelength;
    removing non-cured material;
    deflating said balloon;
    packaging and sterilizing said endoprosthesis and balloon catheter;

inserting said endoprosthesis into the vasculature of a patient;
inflating said balloon proximate a lesion;
curing said prosthesis at a second wavelength;
deflating said balloon;
removing said balloon catheter.

6. The method of claim 5 wherein said predetermined pattern comprises a negative image of an endoprosthesis to be cured in stages on said balloon.

7. The method of claim 5 wherein said first wavelength is in a range of between 320 and 350 nm and said second wavelength is in a range of between 365 and 400 nm.

8. A method of manufacture of an endoprosthesis comprising the steps of
   coextruding a first curable material and a second curable material to form a generally tubular structure;
   cutting portions from said tube to define a desired pattern;
   initiating curing of said first curable material and said second curable material.

9. The method of claim 8 wherein said first curable material cures by exposure to radiation at a first wavelength, and said second curable material cures by exposure to radiation at a second wavelength, and wherein the method further comprises the additional steps of selectively exposing said extruded tube to radiation at said first wavelength, and selectively exposing said extruded tube to radiation at said second wavelength.

10. The method of claim 9 wherein said first wavelength is between 320 and 350 nm and said second wavelength is between 365 and 400 nm.

11. The method of claim 9 wherein the step of selectively exposing said extruded tube to radiation at a first wavelength comprises:
    placing said endoprosthesis within a body lumen;
    providing a balloon catheter and inflating said balloon to nominal pressure;
    introducing a radiation emitting device;
    activating said radiation device to cure material at said first wavelength;
    activating said radiation device to cure material at said second wavelength;
    removing said catheter from said body lumen.

* * * * *